United States Patent
Liu et al.

(10) Patent No.: US 12,227,476 B2
(45) Date of Patent: Feb. 18, 2025

(54) PREPARATION METHOD FOR LEVETIRACETAM INTERMEDIATE

(71) Applicants: ZHEJIANG HUAHAI PHARMACEUTICAL CO., LTD., Zhejiang (CN); ZHEJIANG HUAHAI ZHICHENG PHARMACEUTICAL CO., LTD., Zhejiang (CN); ZHEJIANG HUAHAI TIANCHENG PHARMACEUTICAL CO., LTD, Zhejiang (CN)

(72) Inventors: Bingxin Liu, Zhejiang (CN); Yulong Gong, Zhejiang (CN); Yuanxun Zhu, Zhejiang (CN); Fengfeng Yan, Zhejiang (CN)

(73) Assignee: ZHEJIANG HUAHAI PHARMACEUTICAL CO., LTD., Zhejiang (CN)

( * ) Notice: Subject to any disclaimer, the term of this patent is extended or adjusted under 35 U.S.C. 154(b) by 812 days.

(21) Appl. No.: 17/600,535

(22) PCT Filed: Apr. 17, 2020

(86) PCT No.: PCT/CN2020/085370
§ 371 (c)(1),
(2) Date: Sep. 30, 2021

(87) PCT Pub. No.: WO2020/216146
PCT Pub. Date: Oct. 29, 2020

(65) Prior Publication Data
US 2022/0162165 A1   May 26, 2022

(30) Foreign Application Priority Data
Apr. 23, 2019 (CN) .......................... 201910328462.9

(51) Int. Cl.
*C07D 207/27* (2006.01)
(52) U.S. Cl.
CPC .................................. *C07D 207/27* (2013.01)
(58) Field of Classification Search
CPC .................................................. C07D 207/27
See application file for complete search history.

(56) References Cited

FOREIGN PATENT DOCUMENTS

| CN | 85105301 A | 1/1987 |
|---|---|---|
| CN | 101333180 A | 12/2008 |
| CN | 101838211 A | 9/2010 |
| CN | 104370791 A | 2/2015 |
| CN | 108707099 A | 10/2018 |
| CN | 110003074 A | 7/2019 |
| IN | 200500253 13 | 6/2007 |
| IN | 1546 MU 2005 A | 8/2007 |
| WO | 2006053441 A1 | 5/2006 |

OTHER PUBLICATIONS

Extended European Search Report dated Jun. 15, 2022 in related European Application No. 20795993.3 filed Sep. 10, 2021 (14 pages).
Reddy, K. Chandra Sekhara et al., Racimisation of (R)—Alpha—Ethyl-2-Oxo-!-Pyrrolidine Acetic acid with Thionyl Chloride, Int. J. Pharmaceutical Research Scholars (IJPRS), ISSN No. 2277-7873, V-2, I-1, Jan. 2013, pp. 45-48 (4 pgs).
Neelakandan, K., et al., "An efficient process of racemization of alpha-ethyl-2-oxo-1-pyrrolidineacetic acid: A levetiracetam intermediate", Dec. 31, 2013, Der Pharmacia Sinica, 4(3): pp. 168-172 (5 pages).
Liu, X et al., "Study on the Recovery of Levetiracetam Intermediate LV30 Crystalline Mother Liquor", Shandong Chemical Industry, Aug. 31, 2018, vol. 47 No. 16, pp. 29 and 34 (2 pages) with English abstract on p. 29.
International Search Report and Written Opinion dated Jul. 23, 2020 for corresponding International Application No. PCT/CN2020/085370 filed Apr. 17, 2020 (8 pages) with WIPO machine translation (6 pages).

*Primary Examiner* — Joseph K McKane
*Assistant Examiner* — Jalisa Holmes Ferguson
(74) *Attorney, Agent, or Firm* — Daniel F. Nesbitt; Nesbitt IP LLC

(57) ABSTRACT

A high-quality (RS)-α-ethyl-2-oxo-1-pyrrolidine acetic acid acquired by racemization recovery is provided. A method provided significantly increases the quality and appearance of the product (RS)-α-ethyl-2-oxo-1-pyrrolidine acetic acid recovered using racemization and does not affect the product yield.

6 Claims, 1 Drawing Sheet

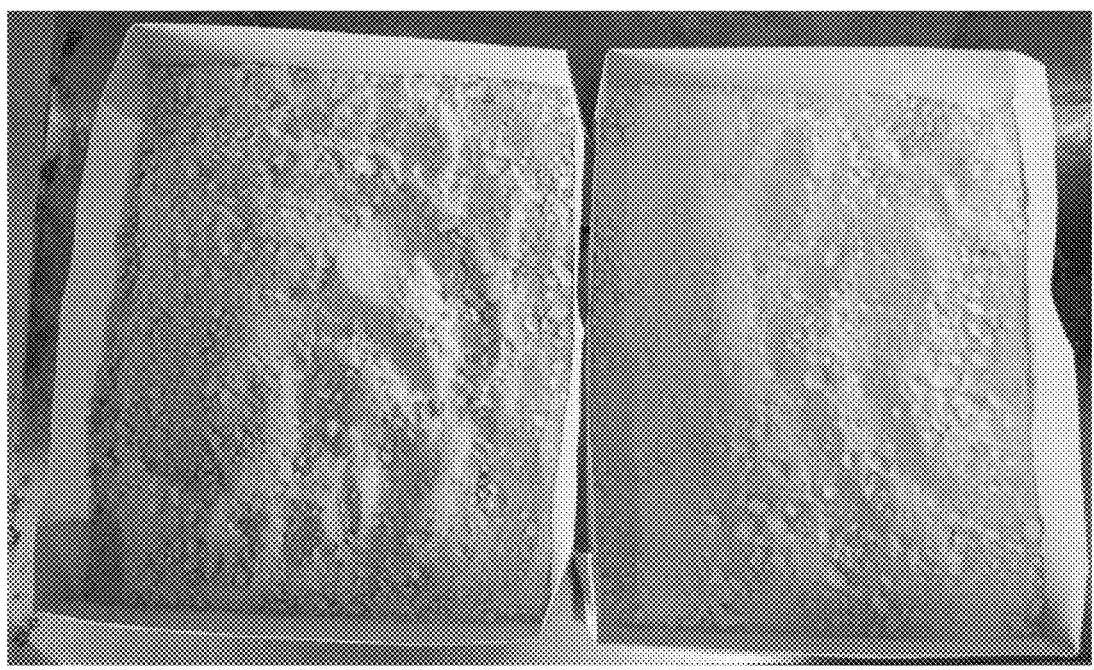

PREPARATION METHOD FOR LEVETIRACETAM INTERMEDIATE

CROSS-REFERENCE TO RELATED APPLICATIONS

This application is a national phase entry of International Application No. PCT/CN2020/085370, filed on Apr. 17, 2020, which claims priority of Chinese Patent Application No. 201910328462.9, filed with the Chinese Patent Office on Apr. 23, 2019, titled PREPARATION METHOD FOR LEVETIRACETAM INTERMEDIATE; which are hereby incorporated by reference in their entireties.

FIELD OF THE INVENTION

The present invention is directed to a preparation method for levetiracetam intermediate, which belongs to a field of medicine and chemical industry.

BACKGROUND OF THE INVENTION

Levetiracetam (trade name Keppra) is a new type of anti-epileptic drug developed by UCB Company in Belgium. It is an acetylpyrrolidine compound with a chemical name of (S)-α-ethyl-2-oxo-1-pyrrolidineacetamide, and its structure is as follows:

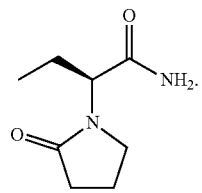

I

CN85105301A discloses a synthetic method of levetiracetam, comprising resolving (±)-α-ethyl-2-oxo-1-pyrrolidineacetic acid (II) to obtain (S)-α-ethyl-2-oxo-1-pyrrolidineacetic acid (III), which is then esterified and ammonolyzed to obtain a crude product of levetiracetam, followed by refining to obtain levetiracetam. The specific synthesis route is as follows:

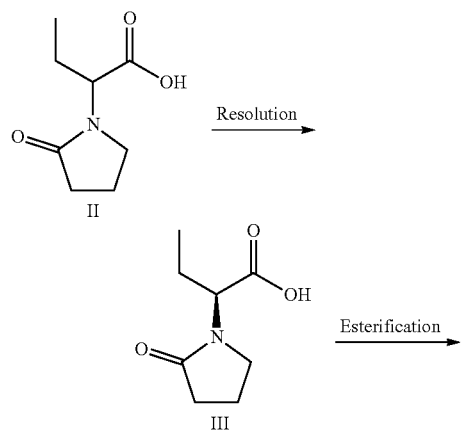

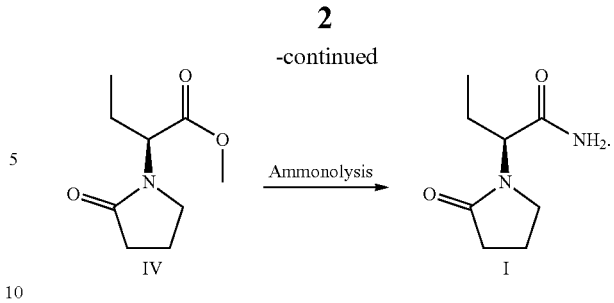

The compound α-ethyl-2-oxo-1-pyrrolidineacetic acid represented by formula II therein is a key intermediate. A small amount of compound III and a large amount of isomer (R)-α-ethyl-2-oxo-1-pyrrolidineacetic acid represented by formula V are present in a mother liquor of the resolution reaction. Patent CN101333180 discloses a method for recovering α-ethyl-2-oxo-1-pyrrolidineacetic acid by high temperature racemization of by-product (R)-α-ethyl-2-oxo-1-pyrrolidine acetic acid.

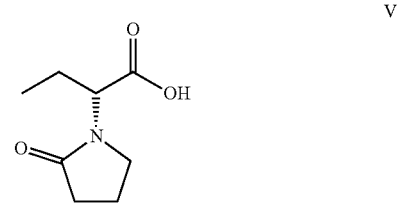

V

However, since the recovery method disclosed in patent CN101333180 is high temperature racemization in the presence of strong base, more impurities will be generated, which will affect the quality of the subsequent production of levetiracetam.

SUMMARY OF THE INVENTION

The present invention is directed to a method for obtaining a high-quality (RS)-α-ethyl-2-oxo-1-pyrrolidineacetic acid (i.e., racemic α-ethyl-2-oxo-1-pyrrolidineacetic acid), comprising the following steps:
(a) adding a mixture comprising (R)-α-ethyl-2-oxo-1-pyrrolidineacetic acid and (S)-α-ethyl-2-oxo-1-pyrrolidineacetic acid to a strong base aqueous solution, heating to 80-95° C. and stirring at this temperature for 8-12 hours;
(b) adding an appropriate amount of water for dilution, cooling to 40-60° C. and adjusting to pH=6.0-8.0 by adding hydrochloric acid dropwise;
(c) adding activated carbon or diatomite for adsorption and decolorization while keeping a temperature of 40-60° C., and then filtering while hot to obtain a filtrate;
(d) heating the filtrate and controlling the temperature in the range of 70-90° C., and adjusting to pH=1.0-2.5 by adding hydrochloric acid dropwise;
(e) cooling to 0-10° C., filtering and drying to obtain (RS)-α-ethyl-2-oxo-1-pyrrolidineacetic acid.

The said mixture comprising (R)-α-ethyl-2-oxo-1-pyrrolidineacetic acid and (S)-α-ethyl-2-oxo-1-pyrrolidineacetic acid in step (a) can be derived from the evaporated dry matter of the mother liquor of the resolution reaction of (RS)-α-ethyl-2-oxo-1-pyrrolidineacetic acid.

The said strong base in step (a) is sodium hydroxide or potassium hydroxide; the mass percentage concentration of the strong base aqueous solution is in the range of 25% to 40%; the amount of the strong base is 1-3 times of the total molar quantity of the mixture comprising (R)-α-ethyl-2-oxo-1-pyrrolidineacetic acid and (S)-α-ethyl-2-oxo-1-pyrrolidineacetic acid.

The amount of water in step (b) is 1.5-5 times of the total mass of the mixture comprising (R)-α-ethyl-2-oxo-1-pyrrolidineacetic acid and (S)-α-ethyl-2-oxo-1-pyrrolidineacetic acid.

The time of the decolorization in step (c) is preferably 0.5 to 1.5 hours.

The innovation of the invention is as follows: through adjusting the pH value to an appropriate range at an appropriate temperature in step (b), unknown impurities generated during the racemization of (R)-α-ethyl-2-oxo-1-pyrrolidineacetic acid in the presence of strong base can be precipitated in the system (the above-mentioned unknown impurities do not show peaks in the whole process of HPLC analysis; if the solution is filtered at this time, a large amount of black solids will appear on filter paper, but the filtrate is still yellow), and the decolorization in step (c) is continued at the temperature of step (b). Through the above operations, the obtained intermediate (RS)-α-ethyl-2-oxo-1-pyrrolidineacetic acid recovered by racemization has excellent quality and appearance while the yield thereof is not affected. Therefore, a risk of introducing unknown impurities into the levetiracetam product is reduced, and an outstanding practical value is obtained.

BRIEF DESCRIPTION OF THE DRAWINGS

In order to explain the examples of the present invention and the technical solutions of the prior art more clearly, the following briefly introduces the figures needed in the examples and the prior art. Obviously, the figures described below are only some examples of the invention. For those skilled in the art, other figures may be obtained based on these figures without creative work.

FIG. 1 is a photograph of the appearance of the Comparative Example and Example 1 of the present application; wherein the left image is the appearance of samples of the Comparative Example, and the right image is the appearance of samples of Example 1 of the present invention.

DETAILED DESCRIPTION OF THE INVENTION

For the sake of clarity of the purpose, technical solutions and advantages of the present invention, the invention is further described in detail in combination with specific figures and examples. Obviously, the described examples are only a part of the examples of the present invention, rather than all the examples. Based on the examples in this invention, all other examples obtained by those of ordinary skill in the art without creative work shall fall within the protection scope of this invention.

Comparative Example 20 g of a dry matter which is obtained by rotary evaporation of the mother liquor of the resolution reaction of (RS)-α-ethyl-2-oxo-1-pyrrolidineacetic acid was added in a four-necked flask, and 23 g of 30% liquid caustic soda (sodium hydroxide) was added to adjust to pH=12-14 to obtain a mixture. The mixture was stirred at 80-95° C. for 8-10 hours to obtain a reaction solution. The reaction solution was added with 100 g of water for dilution, cooled to 60° C., adjusted to pH=1.5 with hydrochloric acid, cooled to 5° C., crystallized and dried to obtain 19.6 g of a recovered (RS)-α-ethyl-2-oxo-1-pyrrolidineacetic acid with a purity of 99.4%. This product color is yellowish. See the left image of FIG. 1.

Example 1

20 g of a dry matter which is obtained by rotary evaporation of the mother liquor of the resolution reaction of (RS)-α-ethyl-2-oxo-1-pyrrolidineacetic acid was added in a four-necked flask, and 45 g of 25% liquid caustic soda (sodium hydroxide) was added to adjust to pH=13-14 to obtain a mixture. The mixture was stirred at 85-95° C. for 8-10 hours to obtain a reaction solution. The reaction solution was added with 100 g of potable water for dilution, cooled to 60° C., and adjusted to pH=7.0 with hydrochloric acid, and a large amount of black brown suspended impurities were appeared in this system. This obtained suspension was added with 0.5 g of activated carbon, stirred at this temperature for 0.5 hour, and suction-filtrated to obtain a filtrate. The filtrate was heated to 70-90° C., added with hydrochloric acid to adjust to pH=1.5 at the temperature, cooled to 0-10° C., crystallized and dried to obtain 19.6 g of a recovered (RS)-α-ethyl-2-oxo-1-pyrrolidineacetic acid with a purity of 99.9%. This product color is white. See the right image of FIG. 1.

Example 2

20 g of a dry matter which is obtained by rotary evaporation of the mother liquor of the resolution reaction of (RS)-α-ethyl-2-oxo-1-pyrrolidineacetic acid was added in a four-necked flask, and 30 g of 30% liquid caustic soda (sodium hydroxide) was added to adjust to pH=12-14 to obtain a mixture. The mixture was stirred at 85-95° C. for 8-10 hours to obtain a reaction solution. The reaction solution was added with 100 g of potable water for dilution, cooled to 60° C., and adjusted to pH=6.0 with hydrochloric acid, and a large amount of black brown suspended impurities were appeared in this system. This obtained suspension was added with 0.5 g of activated carbon, stirred at this temperature for 1.5 hours, and suction-filtrated to obtain a filtrate. The filtrate was heated to 70-90° C., added with hydrochloric acid to adjust to pH=2.0 at the temperature, cooled to 5° C., crystallized and dried to obtain 19.4 g of a recovered (RS)-α-ethyl-2-oxo-1-pyrrolidineacetic acid with a purity of 99.9%. This product color is white.

Example 3

20 g of a dry matter which is obtained by rotary evaporation of the mother liquor of the resolution reaction of (RS)-α-ethyl-2-oxo-1-pyrrolidineacetic acid was added in a four-necked flask, and 16 g of 35% liquid caustic soda (sodium hydroxide) was added to adjust to pH=12-14 to obtain a mixture. The mixture was stirred at 85-95° C. for 8-10 hours to obtain a reaction solution. The reaction solution was added with 100 g of potable water for dilution, cooled to 60° C., and adjusted to pH=6.0 with hydrochloric acid, and a large amount of black brown suspended impurities were appeared in this system. This obtained suspension was added with 0.5 g of medicinal diatomite, stirred at this temperature for 1.0 hour, and suction-filtrated to obtain a filtrate. The filtrate was heated to 70-90° C., added with hydrochloric acid to adjust to pH=1.5 at the temperature, cooled to 5° C., crystallized and dried to obtain 19.5 g of a recovered (RS)-α-ethyl-2-oxo-1-pyrrolidineacetic acid with a purity of 99.7%. This product color is white.

The above are only the preferred examples of the present invention and are not intended to limit this invention. Any modification, equivalent replacement, improvement, etc. made within the spirit and principle of this application shall be included within the scope of protection of this invention.

The invention claimed is:

1. A method for preparing (RS)-α-ethyl-2-oxo-1-pyrrolidineacetic acid, comprising the following steps:
   (a) adding a mixture comprising (R)-α-ethyl-2-oxo-1-pyrrolidineacetic acid and (S)-α-ethyl-2-oxo-1-pyrrolidineacetic acid to a strong base aqueous solution, heating to 80-95° C. and stirring at this temperature for 8-12 hours;
   (b) adding an appropriate amount of water for dilution, cooling to 40-60° C. and adjusting to pH=6.0-8.0 by adding hydrochloric acid dropwise;
   (c) adding activated carbon or diatomite for adsorption and decolorization while keeping a temperature of 40-60° C., and then filtering while hot to obtain a filtrate;
   (d) heating the filtrate and controlling the temperature in the range of 70-90° C., and adjusting to pH=1.0-2.5 by adding hydrochloric acid dropwise; and
   (e) cooling to 0-10° C., filtering and drying to obtain (RS)-α-ethyl-2-oxo-1-pyrrolidineacetic acid.

2. The method according to claim 1, wherein the strong base in step (a) is sodium hydroxide or potassium hydroxide.

3. The method according to claim 1, wherein a mass percentage concentration of the strong base aqueous solution in step (a) is in the range of 25% to 40%.

4. The method according to claim 1, wherein the amount of the strong base in step (a) is 1-3 times of a total molar quantity of the mixture comprising (R)-α-ethyl-2-oxo-1-pyrrolidineacetic acid and (S)-α-ethyl-2-oxo-1-pyrrolidineacetic acid.

5. The method according to claim 1, wherein the amount of water in step (b) is 1.5-5 times of the total mass of the mixture comprising (R)-α-ethyl-2-oxo-1-pyrrolidineacetic acid and (S)-α-ethyl-2-oxo-1-pyrrolidineacetic acid.

6. The method according to claim 1, wherein the time of the decolorization in step (c) is 0.5 to 1.5 hours.

* * * * *